(12) United States Patent
Blakstvedt et al.

(10) Patent No.: US 8,067,024 B2
(45) Date of Patent: Nov. 29, 2011

(54) MEDICAL DEVICES TO PREVENT OR INHIBIT RESTENOSIS

(75) Inventors: Adam Blakstvedt, Big Lake, MN (US); Jesus Casas, Brooklyn Park, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1265 days.

(21) Appl. No.: 11/627,032

(22) Filed: Jan. 25, 2007

(65) Prior Publication Data

US 2007/0191934 A1 Aug. 16, 2007

Related U.S. Application Data

(60) Provisional application No. 60/743,271, filed on Feb. 10, 2006.

(51) Int. Cl.
*A61F 2/02* (2006.01)
*A61K 9/14* (2006.01)
(52) U.S. Cl. ........................... 424/423; 424/489
(58) Field of Classification Search .................. None
See application file for complete search history.

(56) References Cited

U.S. PATENT DOCUMENTS

| 6,547,803 | B2 | 4/2003 | Seward et al. |
| 6,585,764 | B2 | 7/2003 | Wright et al. |
| 2002/0198512 | A1 | 12/2002 | Seward et al. |
| 2003/0055400 | A1 | 3/2003 | Seward et al. |

FOREIGN PATENT DOCUMENTS

| EP | 0623354 | 10/2002 |
| WO | WO97/02285 | 1/1997 |
| WO | WO98/07743 | 2/1998 |

OTHER PUBLICATIONS

Fehr, T.: et al.: J. Antibiot. 1999, 52(5): 474.
Sanglier, J.-J. ; et al., J. Antibiot. 1999 52(5) : 466.
Allen, A. ; et al., J. Immunol. 2004, 172(8): 4797.
Woltman, A.M.; et al., J. Immunol. 2004, 172(10): 6482.
Steinschulte, C.; et al., Am. J. Transplant 2004, 4 (Suppl. 8): Abst. 129.
Nicolaou, K.C.; et al.; "Total Synthesis of the Novel Immunosuppressant Sanglifehrin A" J. Am. Chem. Soc. 2000, 122, pp. 3830-3838.
Zhao L., et al.; "Selective Interleukin-12 Synthesis Defect in 12/15-Lipoxygenase-Deficient Macrophages Associated with Reduced Atherosclerosis in a Mouse Model of Familial Hypercholesterolemia" The Journal of Biological Chemistry, vol. 277, No. 38, Issue of Sep. 20, pp. 35350-35356, 2002.
Nicolaou, K.C., et al. : "Total Synthesis of Sanglifehrin A" Angew. Chem.Int.Ed. 1999, 38, No. 16, pp. 2447-2451. Zhang, L., et al. "Inhibition of Cell Cycle Progression by the Novel Cyclophilin Ligand Sanglifehrin A is Mediated Through the $NF_\kappa B$-Dependent Activation of p53," The Journal of Biological Chemistry, vol. 276, No. 47, Issue of Nov. 23, pp. 43534-43540, 2001.
Clarke, S., et al. "Sanglifehrin A Acts as a Potent Inhibitor of the Mitochondrial Permeability Transition and Reperfusion Injury of the Heart by Binding to Cyclophilin-D at a Different Site from Cyclosporin A," The Journal of Biological Chemistry, vol. 277, No. 38, Issue of Sep. 20, pp. 34793-34799, 2002.

*Primary Examiner* — Carlos Azpuru

(57) ABSTRACT

Implantable medical devices having anti-restenotic coatings are disclosed. Specifically, implantable medical devices having coatings of certain anti-inflammatory agents, are disclosed. The anti-inflammatory agents are selected from the group consisting of Sanglifehrin A, Sanglifehrin B, Sanglifehrin C, Sanglifehrin D, and pharmaceutically acceptable derivatives thereof. The anti-restenotic medical devices include stents, catheters, micro-particles, probes and vascular grafts. Intravascular stents are preferred medical devices. The medical devices can be coated using any method known in the art including compounding the anti-inflammatory agent with a biocompatible polymer prior to applying the coating. Moreover, medical devices composed entirely of biocompatible polymer-anti-inflammatory agent blends are disclosed. Additionally, medical devices having a coating comprising at least one anti-inflammatory agent in combination with at least one additional therapeutic agent are also disclosed. Furthermore, related methods of using and making the anti-restenotic implantable devices are also disclosed.

8 Claims, 1 Drawing Sheet

MEDICAL DEVICES TO PREVENT OR INHIBIT RESTENOSIS

RELATED APPLICATIONS

This application claims the benefit of U.S. Provisional Patent Application 60/743,271 filed Feb. 10, 2006.

FIELD OF THE INVENTION

The present invention relates to medical devices and methods of using medical devices to prevent or inhibit restenosis. Specifically, the present invention relates to stents that provide in situ controlled release delivery of anti-restenotic compounds. More specifically, the present invention provides intravascular stents that provide anti-restenotic effective amounts of certain anti-inflammatory agents, directly to tissues at risk for restenosis.

BACKGROUND OF THE INVENTION

Cardiovascular disease, specifically atherosclerosis, remains a leading cause of death in developed countries. Atherosclerosis is a multifactorial disease that results in a narrowing, or stenosis, of a vessel lumen. Briefly, pathologic inflammatory responses resulting from vascular endothelium injury includes the expression of chemokines and adhesion molecules leading to the migration of monocytes and vascular smooth muscle cells (VSMC) from the sub endothelium into the arterial wall's intimal layer. There the VSMC proliferate and lay down an extracellular matrix causing vascular wall thickening and reduced vessel patency.

Cardiovascular disease caused by stenotic coronary arteries is commonly treated using either coronary artery by-pass graft (CABG) surgery or angioplasty. Angioplasty is a percutaneous procedure wherein a balloon catheter is inserted into the coronary artery and advanced until the vascular stenosis is reached. The balloon is then inflated restoring arterial patency. One angioplasty variation includes arterial stent deployment. Briefly, after arterial patency has been restored, the balloon is deflated and a vascular stent is inserted into the vessel lumen at the stenosis site. After expansion of the stent, the catheter is then removed from the coronary artery and the deployed stent remains implanted to prevent the newly opened artery from constricting spontaneously. An alternative procedure involves stent deployment without prior balloon angioplasty, the expansion of the stent against the arterial wall being sufficient to open the artery, restoring arterial patency. However, balloon catheterization and/or stent deployment can result in vascular injury ultimately leading to VSMC proliferation and neointimal formation within the previously opened artery. This biological process whereby a previously opened artery becomes re-occluded is referred to as restenosis.

Treating restenosis requires additional, generally more invasive, procedures including CABG in severe cases. Consequently, methods for preventing restenosis, or treating incipient forms, are being aggressively pursued. One possible method for preventing restenosis is the administration of anti-inflammatory compounds that block or inhibit the inflammatory response at the site of the injury, including local invasion/activation of monocytes, damage to the endothelium, platelets and coagulation activation, and production of inflammatory agents and mediators, thus preventing the release of factors that may trigger VSMC proliferation and migration. Other potentially anti-restenotic compounds include anti-proliferative agents or other chemotherapeutics including rapamycin and paclitaxel. Rapamycin is generally considered an immunosuppressant best known as an organ transplant rejection inhibitor. However, rapamycin is also used to treat severe yeast infections and certain forms of cancer. Paclitaxel, known by its trade name Taxol®, is used to treat a variety of cancers, most notably breast cancer.

Anti-inflammatory compounds can be toxic when administered systemically in anti-restenotic-effective amounts. Furthermore, the exact cellular functions that must be inhibited and the duration of inhibition needed to achieve prolonged vascular patency (greater than six months) are not presently known. Moreover, it is believed that each drug may require its own treatment duration and delivery rate. Therefore, in situ, or site-specific drug delivery using anti-restenotic coated stents has become the focus of intense clinical investigation.

Recent human clinical studies on stent-based anti-restenotic delivery have centered on rapamycin and paclitaxel. In both cases excellent short-term anti-restenotic effectiveness has been demonstrated. However, side effects including vascular erosion have also been seen. Vascular erosion can lead to stent instability and further vascular injury. Furthermore, the extent of cellular inhibition may be so extensive that normal re-endothelialization will not occur. The endothelial lining is essential for maintaining vascular elasticity and as an endogenous source of nitric oxide. Therefore, there is a need for compounds that exert localized anti-restenotic effects while minimizing vascular and cellular damage in order to ensure the long-term success of drug delivery stents. Inasmuch as inflammatory processes are intimately involved in causing restenosis, it would be desirable to find anti-inflammatory agents that are suitable for coating implantable medical devices such as intravascular stents and that are highly effective in preventing or inhibiting restenosis when delivered locally, while being safe for the patient.

SUMMARY OF THE INVENTION

The present invention provides an in situ drug delivery platform that can be used to administer anti-restenotic tissue levels of certain anti-inflammatory agents in a site-specific, controlled release manner, without systemic side effects. It has been found that certain anti-inflammatory agents are highly effective at preventing or inhibiting restenosis when delivered locally to vascular tissue at risk of restenosis. In one embodiment of the present invention the anti-inflammatory agents selected from the group consisting of Sanglifehrin A, Sanglifehrin B, Sanglifehrin C, Sanglifehrin D, and the pharmaceutically acceptable derivatives thereof, are particularly effective for this purpose.

In another embodiment of the present invention the drug delivery platform is an implantable medical device including, without limitation, intravascular stents, catheters, perivascular drug injection catheters or transvascular micro syringes for adventitial drug delivery, and vascular grafts.

In another embodiment of the present invention, an intravascular stent is directly coated with an anti-inflammatory agent selected from the group consisting of Sanglifehrin A, Sanglifehrin B, Sanglifehrin C, Sanglifehrin D, and pharmaceutically acceptable derivatives thereof, hereinafter individually referred to as "anti-inflammatory agent" or collectively referred to as "Sanglifehrins" or "anti-inflammatory agents." The anti-inflammatory agent can be attached to the vascular stent's surface using any means that provide a drug-releasing platform. Coating methods include, but are not limited to precipitation, coacervation, and crystallization. The anti-inflammatory agent of the present invention can be bound covalently, ionically, or through other molecular interactions including, without limitation, hydrogen bonding and van der Waals forces.

In another embodiment of the present invention the anti-inflammatory agent is complexed with a suitable biocompatible polymer. The polymer-drug complex is then used to either form a controlled-release medical device, integrated into a preformed medical device or used to coat a medical device. The biocompatible polymer may be any non-thrombogenic material that does not cause a clinically relevant adverse response. Other methods of achieving controlled drug release are contemplated as being part of the present invention.

Moreover, the anti-inflammatory agents of the present invention can be combined with other anti-restenotic compounds including anti-platelet, anti-thrombotic, anti-oxidant, cytotoxic, cytostatic, anti-metabolic and other anti-proliferative compounds.

In yet another embodiment of the present invention an anti-restenotic compound-coated intravascular stent can be combined with the systemic delivery of the same or another anti-restenotic compound to achieve a synergistic or additive effect at the medical device placement site. This is particularly beneficial in that non-toxic therapeutic levels of the anti-inflammatory agents of the present invention and other anti-restenotic therapeutics can be combined to achieve dose-specific synergism.

In one embodiment of the present invention the anti-inflammatory agent is directly coated onto the surface of a metal stent.

In another embodiment of the present invention the stent is coated with a bioerodible polymer having the anti-inflammatory agent dispersed therein.

In another embodiment of the present invention the stent is coated with a non-bioerodible polymer having the anti-inflammatory agent dispersed therein.

In yet another embodiment of the present invention a stent is coated with a first polymer layer having the anti-inflammatory agent dispersed therein and a second layer of polymer provided over the first polymer layer.

In yet another embodiment of the present invention a stent is provided with an anti-inflammatory agent coating and at least one other antiplatelet, antimigratory, antifibrotic, and/or anti-proliferative agent combined therewith.

In yet another embodiment of the present invention the stent is selected from the group consisting of intravascular stents, biliary stents, esophageal stents, and urethral stents.

In yet another embodiment of the present invention the stent is a metallic stent.

In still another embodiment of the present invention the stent is a polymer stent.

In another embodiment of the present invention there is provided a method for treating or inhibiting restenosis by providing an intravascular stent having a coating comprising an anti-inflammatory agent and implanting the stent in a blood vessel lumen at risk for restenosis wherein the anti-inflammatory agent is released into tissue adjacent the blood vessel lumen.

In yet another embodiment of the present invention there is provided a method for producing a medical device by providing a medical device to be coated, compounding an anti-inflammatory agent with a carrier compound, and coating the medical device with the anti-inflammatory agent compounded with the carrier compound.

Additional embodiments of the present invention will be apparent to those skilled in the art from the drawings and detailed disclosure that follows.

DETAILED DESCRIPTION OF THE PRESENT INVENTION

Figure 1:
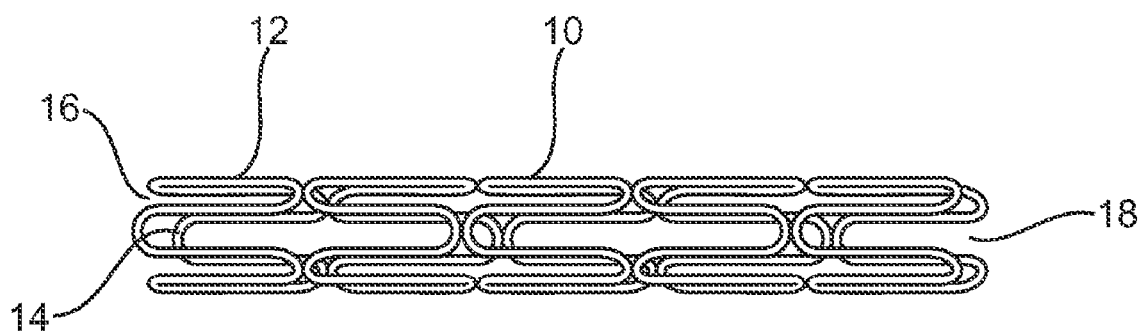
FIG. 1 depicts an intravascular stent used to deliver the antirestenotic compounds of the present invention.

The present invention relates to restoring patency to anatomical lumens that have been occluded, or stenosed, as a result of mechanical trauma, surgical injury, pathologies or normal biological processes including genetic anomalies. The present invention can be used to restore and maintain patency in any anatomical lumen, including, but not limited to blood vessels, ducts such as the biliary duct, and wider lumens including the esophagus and urethra. Furthermore, graft site associated stenoses can also be treated using the teachings of the present invention.

In one embodiment of the present invention the stenosed lumen is an artery, specifically a coronary artery. Stenosed coronary arteries generally result from plaque that develops on the interior lining of a coronary artery. Present models attribute this pathology to vascular injuries that are associated with life style and diet. Two major categories of vascular plaque are thought to contribute to over 90% of coronary artery disease (CAD): vulnerable plaque and stable plaque. While both plaque types can contribute to stenosis requiring intervention consistent with the teachings of the present invention, vulnerable plaque is more frequently associated with sudden coronary death resulting from plaque rupture and the associated thrombogenic processes, rather than with stenosis. Stable plague is not prone to rupture due to the presence of a thick fibrous cap and less amorphous, more stable, smaller lipid core than found in vulnerable plaque, and is more amenable to angioplasty and stent deployment. Therefore, the majority of vascular stenoses requiring intervention are associated with stable plaque.

In one embodiment of the present invention percutaneous transluminal coronary angioplasty (PTCA), or balloon angioplasty, is used to correct stenoses found in coronary, iliac or kidney arteries, followed by stent deployment. Stents are mesh-like structures or coils that are mounted to an angioplasty balloon for expansion, or are self-expanding, and are permanently placed in the artery or vein following PTCA.

In the typical procedure a patient is brought to the cardiac catheterization lab where intravenous fluids and medications are administered prior to beginning PTCA. Patients may also receive intravenous sedation to provide some comfort and anxiety relief. Next arterial and venous punctures are made and a sheath is inserted to provide access to the vascular system for a guidewire and coronary catheter. The coronary catheter is advanced over the guidewire and gently brought near the orifice of the coronary arteries. The guidewire is then removed and intravenous x-ray contrast dye is injected into the coronary arteries to facilitate visualizing the exact location of the stricture and the degree of narrowing. The patient's blood pressure, heart rate, electrocardiogram, and oxygen saturation are monitored continuously.

If severe stenosis of the coronary arteries is identified, an angioplasty balloon is inflated to dilate the stenosed region and a vascular stent is deployed to prevent immediate tissue elastic recoil and arterial re-occlusion. Exact stent placement is confirmed using repeat x-rays and when appropriate, intracoronary ultrasound. One of the major complications associated with vascular stenting is restenosis. Restenosis results from injury to the vascular endothelium associated PTCA and stenting procedures. Briefly, the process of inflating the balloon catheter can tear the vessels' intimal layer of endothelial cells. The damaged endothelial cells secrete chemokines and adhesion molecules causing monocytes and vascular smooth muscle cells (VSMCs) to migrate from the sub endothelium into the arterial wall's intimal layer. Studies have shown that the extent of intimal development after stenting is directly related to the numbers of inflammatory cells recruited to the stent.

Other embodiments of the present invention include stenting procedures for peripheral vascular disease, such as, but not limited to, iliac artery stenosis, renal hypertension due to severe renal artery stenosis, and carotid artery stenosis. Moreover, neurovascular applications of the present invention are also considered within the scope of the present invention.

It has been surprisingly found that certain compounds are particularly effective in the prevention or inhibition of restenosis. In the detailed description and claims that follow, these compounds used to prevent restenosis may be referred to herein or elsewhere individually as an "anti-inflammatory agent" or collectively as "Sanglifehrins" or "anti-inflammatory agents." The anti-inflammatory agents of the present invention are selected from the group consisting of Sanglifehrin A, Sanglifehrin B, Sanglifehrin C, Sanglifehrin D, and pharmaceutically acceptable derivatives thereof.

Sanglifehrin A has the chemical name (3S,6S,9R,10R,11S, 12S,18S,21S)-18-[(1E,3E,7S,8S)-9-[(2S,3R,4S,5S,6R,9S, 11S)-9-Ethyl-4-hydroxy-3,5,11-trimethyl-8-oxo-1-oxa-7-azaspiro[5.5]undec-2-yl]-8-hydroxy-1,7-dimethyl-1,3-nonadienyl]-10,12-dihydroxy-3-(3-hydroxybenzyl)-6-isopropyl-11-methyl-9-(3-oxobutyl)-19-oxa-1,4,7,25-tetraazabicyclo[19.3.1]pentacosa-13,15-diene-2,5,8,20-tetrone and has the structural formula as depicted in Formula 1.

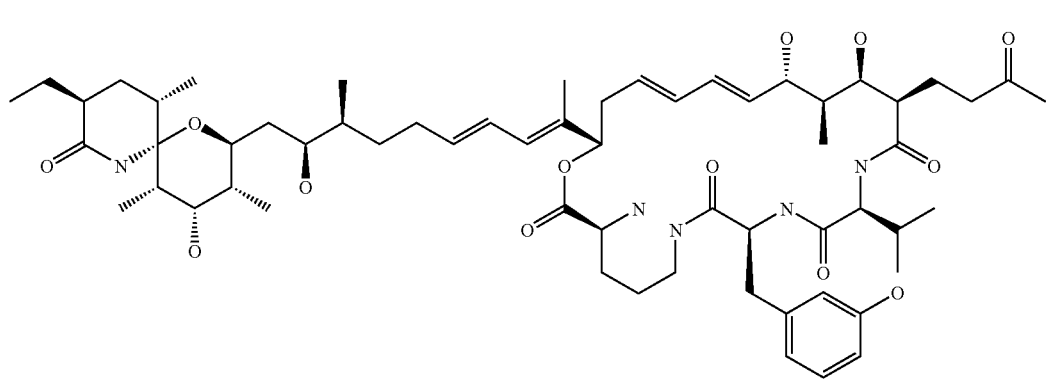

Formula 1

Sanglifehrin B has the chemical name (3S,6S,9R,10R,11S, 12S,18S,21S)-18-[(1E,3E,7S,8S)-9-[(2S,3R,6R,9S,11S)-9-Ethyl-3,5,11-trimethyl-8-oxo-1-oxa-7-azaspiro[5.5]undec-4-en-2-yl]-8-hydroxy-1,7-dimethyl-1,3-nonadienyl]-10,12-dihydroxy-3-(3-hydroxybenzyl)-6-isopropyl-11-methyl-9-(3-oxobutyl)-19-oxa-1,4,7,25-tetraazabicyclo[19.3.1]pentacosa-13,15-diene-2,5,8,20-tetrone and has the structural formula as depicted in Formula 2.

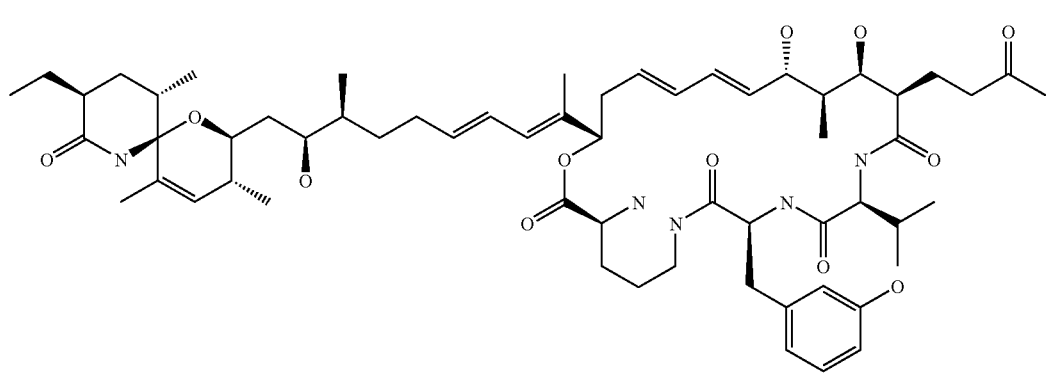

Formula 2

Sanglifehrin C has the chemical name (3S,6S,9R,12S,14R,15S,16S,22S,25S)-22-[(1E,3E,7S,8S)-9-[(2S,3R,4S,5S,6R,9S,11S)-9-Ethyl-4-hydroxy-3,5,11-trimethyl-8-oxo-1-oxa-7-azaspiro[5.5]undec-2-yl]-8-hydroxy-1,7-dimethyl-1,3-nonadienyl]-16-hydroxy-3-(3-hydroxybenzyl)-6-isopropyl-12-methoxy-12,15-dimethyl-13,23-dioxa-1,4,7,29-tetraazatricyclo[23.3.1.0~9,14~]nonacosa-17,19-diene-2,5,8,24-tetrone and has the structural formula as depicted in Formula 3.

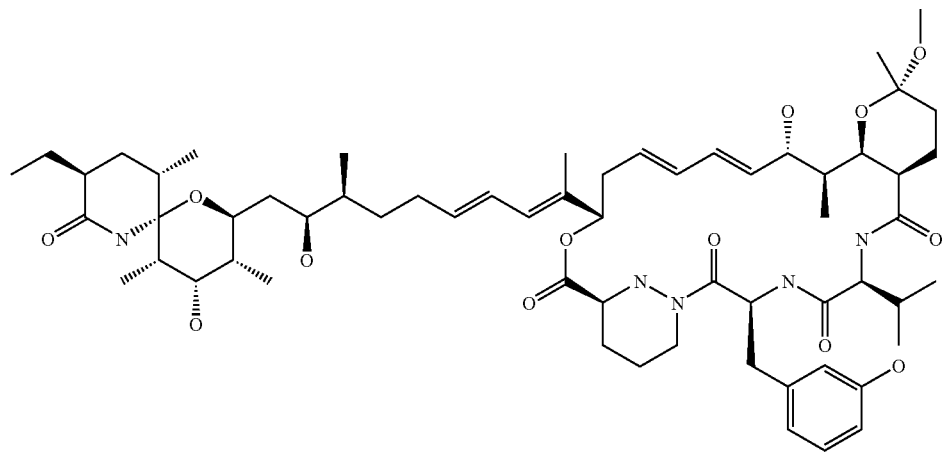

Formula 3

Sanglifehrin D has the chemical name (3S,6S,9R,12S,14R,15S,16S,22S,25S)-22-[(1E,3E,7S,8S)-9-[(2S,3R,6R,9S,11S)-9-ethyl-3,5,11-trimethyl-8-oxo-1-oxa-7-azaspiro[5.5]undec-4-en-2-yl]-8-hydroxy-1,7-dimethyl-1,3-nonadienyl]-16-hydroxy-3-(3-hydroxybenzyl)-6-isopropyl-12-methoxy-12,15-dimethyl-13,23-dioxa-1,4,7,29-tetraazatricyclo[23.3.1.0~9,14~]nonacosa-17,19-diene-2,5,8,24-tetrone and has the structural formula as depicted in Formula 4.

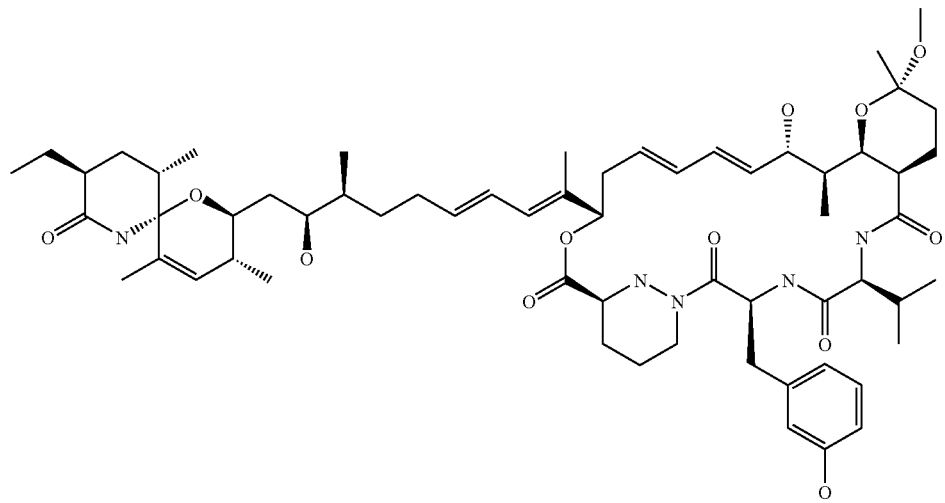

Formula 4

All of the names and terms for each of the above compounds of the present invention may be used interchangeably without distinction and are all considered to be within the scope of the present invention.

Sanglifehrins A, B, C and D are macrolide anti-inflammatory agents isolated from *Streptomyces* sp. A92-308110 and are being developed by Novartis as immunosuppressive agents. They are further described in the references cited below and incorporated by reference herein.

Neo-intima formation resulting from VSMC proliferation at the site of vascular injury accounts for the majority of non-elastic recoil restenosis. Physical stress applied to the stenosed artery's intimal lining during angioplasty often results in rupture of the endothelial layer and damage to the underlying VSMC layer. The associated cell injury triggers a cascade of events that cause the VSMCs to de-differentiate and proliferate through the damaged intima re-occluding the artery. The compounds of the present invention are believed to act as anti-inflammatory agents having a variety of mechanisms of action such as inhibitors of cell adhesion, NF-kappaB modulators, TNF inhibitors, inhibitors of inflammation related MAPKs such as p38 and JNK, MMP inhibitors, activity toward chemokines and their receptors, anti-oxidants or combinations of the above. All of these are believed to be ultimately responsible for inhibiting proliferation and migration of VSMC and the production of inflammatory cytokines by macrophages.

Without being bound by any particular mechanisms of action, it is believed that the above mechanistic descriptions portray how the compounds of the present invention function as anti-restenotic agents.

The present invention includes novel compositions and methods for delivering anti-inflammatory agents directly to tissues susceptible to restenosis. Specifically, the present invention is directed at implantable medical devices, preferably intravascular stents, which provide for the in situ, site-specific, controlled release of drugs that inhibit inflammation and vascular smooth muscle cell (VSMC) proliferation.

In one embodiment of the present invention medical devices are provided with an anti-inflammatory agent selected from the group consisting of Sanglifehrin A, Sanglifehrin B, Sanglifehrin C, Sanglifehrin D, and the pharmaceutically acceptable derivatives thereof.

In another embodiment of the present invention the anti-inflammatory agent is Sanglifehrin A or a pharmaceutically acceptable derivative thereof.

In another embodiment of the present invention the anti-inflammatory agent is Sanglifehrin B or a pharmaceutically acceptable derivative thereof.

In another embodiment of the present invention the anti-inflammatory agent is Sanglifehrin C or a pharmaceutically acceptable derivative thereof.

In another embodiment of the present invention the anti-inflammatory agent is Sanglifehrin D or a pharmaceutically acceptable derivative thereof.

It will be understood by those skilled in the art that many isomers, salts, analogs and other derivatives are also possible that do not affect the efficacy or mechanism of action of the anti-inflammatory agents of the present invention. Therefore, the present invention is intended to encompass Sanglifehrin A, Sanglifehrin B, Sanglifehrin C, Sanglifehrin D, and pharmaceutically acceptable derivatives thereof. The term "pharmaceutically acceptable derivatives" as used herein includes all derivatives, analogs, enantiomers, diastereomers, stereoisomers, free acids and bases, and acid and base addition salts, as the case may be, that are not substantially toxic at anti-restenotic-effective levels in vivo. "Not substantially toxic" as used herein shall mean systemic or localized toxicity wherein the benefit to the recipient out-weighs the physiologically harmful effects of the treatment as determined by physicians and pharmacologists having ordinary skill in the art of chemotherapy and toxicology. Pharmaceutically acceptable salts include, without limitation, salts formed with inorganic or organic acids or bases commonly used for pharmaceutical purposes.

The anti-inflammatory agents of the present invention may be delivered, alone or in combination with synergistic and/or additive therapeutic agents, directly to the affected area using medical devices. Potentially synergistic and/or additive therapeutic agents may include drugs that impact a different aspect of the restenosis process such as antiplatelet, antimigratory or antifibrotic agents. Alternately they may include drugs that also act as anti-proliferatives. For example, and not intended as a limitation, synergistic combination, considered to within the scope of the present invention include at least one anti-inflammatory agent and an antisense anti-c-myc oligonucleotide, at least one anti-inflammatory agent and rapamycin or analogues and derivatives thereof such a 40-0-(2-hydroxyethyl)-rapamycin, at least one anti-inflammatory agent and exochelin, at least one anti-inflammatory agent and an N-acetyl cysteine inhibitor, and so on.

The medical devices used in accordance with the teachings of the present invention may be permanent medical implants, temporary implants, or removable implantable devices. For example, and not intended as a limitation, the medical devices of the present invention may include, intravascular stents, catheters, perivascular drug injection catheters or transvascular micro syringes, and vascular grafts.

In one embodiment of the present invention stents are used as the drug delivery platform. The stents may be intravascular stents, urethral stents, biliary stents, or stents intended for use in other ducts and organ lumens. Vascular stents may be used in peripheral, neurological or coronary applications. The stents may be rigid expandable stents or pliable self-expanding stents. Any biocompatible material may be used to fabricate the stents of the present invention including, without limitation, metals or polymers. The stents of the present invention may also be bioresorbable.

In one embodiment of the present invention intravascular stents are implanted into coronary arteries immediately following angioplasty. However, one significant problem associated with stent implantation, specifically intravascular stent deployment, is restenosis. Restenosis is a process whereby a previously opened lumen is re-occluded by VSMC proliferation. Therefore, it is an object of the present invention to provide stents that suppress or eliminate VSMC migration and proliferation and thereby reduce, and/or prevent restenosis.

In one embodiment of the present invention metallic intravascular stents are coated with one or more anti-restenotic compounds, specifically at least one anti-inflammatory agent of the present invention. The anti-inflammatory agent may be dissolved or suspended in any carrier compound that provides a stable composition that does not react adversely with the device to be coated or inactivate the anti-inflammatory agent. The metallic stent is provided with a biologically active anti-inflammatory agent coating using any technique known to those skilled in the art of medical device manufacturing. Suitable non-limiting examples include impregnating, spraying, brushing, dipping, rolling and electrostatic deposition. After the anti-inflammatory agent solution is applied to the stent it is dried leaving behind a stable anti-inflammatory agent-delivering medical device. Drying techniques include, but are not limited to, heated forced air, cooled forced air, vacuum drying or static evaporation.

The anti-restenotic effective amounts of anti-inflammatory agents used in accordance with the teachings of the present invention can be determined by a titration process. Titration is accomplished by preparing a series of stent sets. Each stent set will be coated, or contain different dosages of the anti-inflammatory agent selected. The highest concentration used will be partially based on the known toxicology of the compound. The maximum amount of drug delivered by the stents made in accordance with the teaching of the present invention will fall below known toxic levels. Each stent set will be tested in vivo using the preferred animal model as described in Example 5 below. The dosage selected for further studies will be the minimum dose required to achieve the desired clinical outcome. In the case of the present invention, the desired clinical outcome is defined as the inhibition of vascular re-occlusion, or restenosis. Generally, and not intended as a limitation, an anti-restenotic effective amount of the anti-inflammatory agents of the present invention will range between about 0.5 ng and 1.0 mg, most preferably between about 10 µg and 1.0 mg, depending on the particular anti-inflammatory agent used and the delivery platform selected.

In addition to the anti-inflammatory agent selected, treatment efficacy may also be affected by factors including dosage, route of delivery and the extent of the disease process (treatment area). An effective amount of an anti-inflammatory agent composition can be ascertained using methods known to those having ordinary skill in the art of medicinal chemistry and pharmacology. First the toxicological profile for a given anti-inflammatory agent composition is established using standard laboratory methods. For example, the candidate anti-inflammatory agent composition is tested at various concentrations in vitro using cell culture systems in order to determine cytotoxicity. Once a non-toxic, or minimally toxic, concentration range is established, the anti-inflammatory agent composition is tested throughout that range in vivo using a suitable animal model. After establishing the in vitro and in vivo toxicological profile for the anti-inflammatory agent, it is tested in vitro to ascertain if the compound retains anti-inflammatory activity at the non-toxic, or minimally toxic ranges established.

Finally, the candidate anti-inflammatory agent composition is administered to treatment areas in humans in accordance with either approved Food and Drug Administration (FDA) clinical trial protocols, or protocol approved by Institutional Review Boards (IRB) having authority to recommend and approve human clinical trials for minimally invasive procedures. Treatment areas are selected using angiographic techniques or other suitable methods known to those having ordinary skill in the art of intervention cardiology. The candidate anti-inflammatory agent composition is then applied to the selected treatment areas using a range of doses. Preferably, the optimum dosages will be the highest non-toxic, or minimally toxic concentration established for the anti-inflammatory agent composition being tested. Clinical follow-up will be conducted as required to monitor treatment efficacy and in vivo toxicity. Such intervals will be determined based on the clinical experience of the skilled practitioner and/or those established in the clinical trial protocols in collaboration with the investigator and the FDA or IRB supervising the study.

The anti-inflammatory agent therapy of the present invention can be administered directly to the treatment area using any number of techniques and/or medical devices. In one embodiment of the present invention the anti-inflammatory agent composition is applied to an intravascular stent. The intravascular stent can be of any composition or design. For example, the stent may be a self-expanding stent 10 depicted in FIG. 1, or a balloon-expandable stent 10 depicted in FIG. 1, expanded using a balloon catheter depicted in FIG. 2. The medical device can be made of virtually any biocompatible material having physical properties suitable for the design. For example, tantalum, stainless steel, nickel alloys, chromium alloys, titanium alloys and cobalt alloys have been proven suitable for many medical devices and could be used in the present invention. A cobalt alloy such as that used in the Driver® coronary stent of Medtronic Vascular, Inc. is particularly useful for this purpose. Also, medical devices made with biostable or bioabsorbable polymers can be used in accordance with the teachings of the present invention. In yet other embodiments the Anti-inflammatory agent therapy of the present invention is delivered using a porous or "weeping" catheter to deliver an anti-inflammatory agent-containing hydrogel composition to the treatment area. Still other embodiments include microparticles or other forms delivered using a catheter such as a perivascular drug injection catheter or transvascular micro syringe for adventitial delivery, or other intravascular or transmyocardial device.

In one embodiment of the present invention an injection catheter as depicted in U.S. patent application publication No. 2002/0198512 A1, U.S. patent application Ser. No. 09/961,079 and U.S. Pat. No. 6,547,803 (all of which are herein incorporated by reference in their entirety, specifically those sections directed to adventitial delivery of pharmaceutical compositions) can be used to administer the antibodies of the present invention directly to the adventitia.

Figure 2:
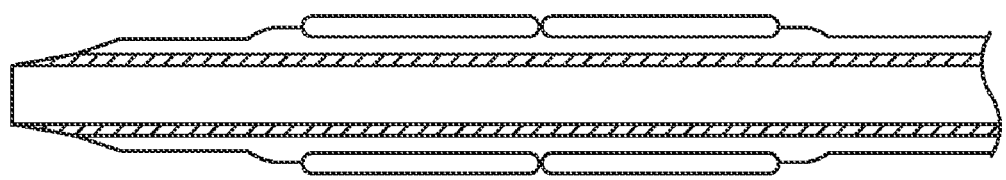
FIG. 2 depicts a balloon catheter assembly used for angioplasty and the site-specific delivery of stents to anatomical lumens at risk for restenosis.

Although the medical device surface should be clean and free from contaminants that may be introduced during manufacturing, the medical device surface requires no particular surface treatment in order to retain the coating applied in the present invention. With reference to FIG. 1, both surfaces (inner 14 and outer 12 of stent 10, or top and bottom depending on the medical device's configuration) of the medical device may be provided with the coating according to the present invention.

In order to provide the coated medical device according to the present invention, a solution that includes a solvent, a polymer dissolved in the solvent and a Anti-inflammatory agent composition dispersed in the solvent is first prepared. It is important to choose a solvent, a polymer and a therapeutic substance that are mutually compatible. It is essential that the solvent is capable of placing the polymer into solution at the concentration desired in the solution. It is also essential that the solvent and polymer chosen do not chemically alter the anti-inflammatory agent's therapeutic character. However, the anti-inflammatory agent composition only needs to be dispersed throughout the solvent so that it may be either in a true solution with the solvent or dispersed in fine particles in the solvent. The solution is applied to the medical device and the solvent is allowed to evaporate leaving a coating on the medical device comprising the polymer(s) and the anti-inflammatory agent composition.

Typically, the solution can be applied to the medical device by either spraying the solution onto the medical device or immersing the medical device in the solution. Whether one chooses application by immersion or application by spraying depends principally on the viscosity and surface tension of the solution, however, it has been found that spraying in a fine spray such as that available from an airbrush will provide a coating with the greatest uniformity and will provide the greatest control over the amount of coating material to be applied to the medical device. In either a coating applied by spraying or by immersion, multiple application steps are generally desirable to provide improved coating uniformity and improved control over the amount of Anti-inflammatory agent composition to be applied to the medical device. See, for example, European Patent No. 0623354 to Medtronic, Inc. The total thickness of the polymeric coating will range from about 0.1 micron to about 100 microns, preferably between about 1 micron and 20 microns. The coating may be applied in one coat or, preferably, in multiple coats, allowing each coat to substantially dry before applying the next coat. In one embodiment of the present invention the anti-inflammatory agent composition is contained within a base coat, and a top coat containing only polymer is applied over the anti-inflammatory agent-containing base coat to control release of the anti-inflammatory agent into the tissue and to protect the base coat during handling and deployment of the stent. The coating may be of the entire medical device or to selected portions thereof, including grooves, holes, recesses, or other macroscopic features thereof that are amenable to drug deposition and coating, such as those disclosed in patents to Conormed, Inc., to de Scheerder and in U.S. Pat. No. 6,585,764 to Wright et al.

The polymer chosen must be a polymer that is biocompatible and minimizes irritation to the vessel wall when the medical device is implanted. It must also exhibit high elasticity/ductility, resistance to erosion, elasticity, and controlled drug release. The polymer may be either a biostable or a bioabsorbable polymer depending on the desired rate of release or the desired degree of polymer stability. Bioabsorbable polymers that could be used include poly(L-lactic acid), polycaprolactone, poly(lactide-co-glycolide), poly(ethylene-vinyl acetate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid.

Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

The polymer-to-anti-inflammatory agent composition ratio will depend on the efficacy of the polymer in securing the anti-inflammatory agent composition onto the medical device and the rate at which the coating is to release the anti-inflammatory agent composition to the tissue of the blood vessel. More polymer may be needed if it has relatively poor efficacy in retaining the anti-inflammatory agent composition on the medical device and more polymer may be needed in order to provide an elution matrix that limits the elution of a very soluble anti-inflammatory agent composition. A wide ratio of therapeutic substance-to-polymer could therefore be appropriate and could range from between about 10:1 to about 1:100, preferably between about 1:1 to about 1:10 (w/w).

In one embodiment of the present invention a vascular stent as depicted in FIG. 1 is coated with an anti-inflammatory agent selected from the group consisting of Sanglifehrin A, Sanglifehrin B, Sanglifehrin C, Sanglifehrin D, and pharmaceutically acceptable derivatives thereof, using a two-layer biologically stable polymeric matrix comprised of a base layer and an outer layer. Stent 10 has a generally cylindrical shape and an outer surface 12, an inner surface 14, a first open end 16, a second open end 18 and wherein the outer and inner surfaces 12, 14 are adapted to deliver an anti-restenotic effective amount of at least one anti-inflammatory agent in accordance with the teachings of the present invention. Briefly, a polymer base layer comprising a solution of ethylene-co-vinylacetate and polybutylmethacrylate is applied to stent 10 such that the outer surface 12 is coated with polymer. In another embodiment both the inner surface 14 and outer surface 12 of stent 10 are provided with polymer base layers. The Anti-inflammatory agent or mixture thereof is incorporated into the base layer. Next, an outer layer comprising only polybutylmethacrylate is applied to stent 10 outer layer 14 that has been previous provide with a base layer. In another embodiment both the inner surface 14 and outer surface 12 of stent 10 are proved with polymer outer layers.

The thickness of the polybutylmethacrylate outer layer determines the rate at which the Anti-inflammatory agents elute from the base coat by acting as a diffusion barrier. The ethylene-co-vinylacetate, polybutylmethacrylate and anti-inflammatory agent solution may be incorporated into or onto a medical device in a number of ways. In one embodiment of the present invention the anti-inflammatory agent/polymer solution is sprayed onto the stent 10 and then allowed to dry. In another embodiment, the solution may be electrically charged to one polarity and the stent 10 electrically changed to the opposite polarity. In this manner, the anti-inflammatory agent/polymer solution and stent will be attracted to one another thus reducing waste and providing more control over the coating thickness.

In another embodiment of the present invention the anti-inflammatory agent is selected from the group consisting of Sanglifehrin A, Sanglifehrin B, Sanglifehrin C, Sanglifehrin D, and pharmaceutically acceptable derivatives thereof, and the polymer is bioresorbable. The bioresorbable polymer-anti-inflammatory agent blends of the present invention can be designed such that the polymer absorption rate controls drug release. In one embodiment of the present invention a polycaprolactone-anti-inflammatory agent blend is prepared. A stent 10 is then stably coated with the polycaprolactone-anti-inflammatory agent blend wherein the stent coating has a thickness of between about 0.1 micron and 100 microns, preferably between about 1 micron and 20 microns. The polymer coating thickness determines the total amount of anti-inflammatory agent delivered and the polymer's absorption rate determines the administration rate.

Using the preceding guidelines it is possible for one of ordinary skill in the part of polymer chemistry to design coatings having a wide range of dosages and administration rates. Furthermore, drug delivery rates and concentrations can also be controlled using non-polymer containing coatings and techniques known to persons skilled in the art of medicinal chemistry and medical device manufacturing, The following examples are provided to more precisely define and enable the anti-inflammatory agent-eluting medical devices of the present invention. It is understood that there are numerous other embodiments and methods of using the present invention that will be apparent to those of ordinary skill in the art after having read and understood this specification and examples. These alternate embodiments are considered part of the present invention.

EXAMPLES

Providing a Metallic Surface with a Anti-Inflammatory Agent-Eluting Coating

The following Examples are intended to illustrate a non-limiting process for coating metallic stents with an anti-inflammatory agent and testing their anti-restenotic properties. One non-limiting example of a metallic stent suitable for use in accordance with the teachings of the present invention is the Medtronic Vascular, Inc. Driver® cobalt alloy coronary stent.

Example 1

Metal Stent Cleaning Procedure

Medtronic Vascular, Inc. Driver® cobalt alloy coronary stents were placed in a glass beaker and covered with reagent grade or better hexane. The beaker containing the hexane-immersed stents was then placed into an ultrasonic water bath and treated for 15 minutes at a frequency of between approximately 25 to 50 KHz. Next the stents were removed from the hexane and the hexane was discarded. The stents were then immersed in reagent grade or better 2-propanol and vessel containing the stents and the 2-propanol was treated in an ultrasonic water bath as before. Following cleaning the stents with organic solvents, they were thoroughly washed with distilled water and thereafter immersed in 1.0 N sodium hydroxide solution and treated at in an ultrasonic water bath as before. Finally, the stents were removed from the sodium hydroxide, thoroughly rinsed in distilled water and then dried in a vacuum oven overnight at 40° C.

After cooling the dried stents to room temperature in a desiccated environment they were weighed their weights were recorded.

Example 2

Coating a Clean, Dried Stent Using a Drug/Polymer System

In the following Example chloroform or tetrahydrofuran is chosen as the solvent of choice. Both the polymer and the anti-inflammatory agents are freely soluble in these solvents. Persons having ordinary skill in the art of polymer chemistry can easily pair the appropriate solvent system to the polymer-drug combination and achieve optimum results with no more than routine experimentation.

250 mg of Sanglifehrin A is carefully weighed and added to a small neck glass bottle containing 2.8 ml of chloroform or tetrahydrofuran and thoroughly mixed until a clear solution is achieved.

Next 250 mg of polycaprolactone (PCL) is added to the Sanglifehrin A solution and mixed until the PCL dissolved forming a drug/polymer solution.

The cleaned, dried stents are coated using either spraying techniques or dipped into the drug/polymer solution. The stents are coated as necessary to achieve a final coating (drug plus polymer) weight of between about 10 μg and 1.0 mg. Finally, the coated stents are dried in a vacuum oven at 50° C. overnight. The dried, coated stents are weighed and the weights recorded.

The concentration of drug loaded onto the stents is determined based on the final coating weight. Final coating weight is calculated by subtracting the stent's pre-coating weight from the weight of the dried, coated stent.

In a similar manner, Sanglifehrin A may be replaced by similar quantities of Sanglifehrin B, Sanglifehrin C, Sanglifehrin D, or pharmaceutically acceptable derivatives thereof.

Example 3

Coating a Clean, Dried Stent Using a Sandwich-Type Coating

A cleaned, dry stent is first coated with polyvinyl pyrrolidone (PVP) or another suitable polymer followed by a coating of Sanglifehrin A. Finally, a second coating of PVP is provided to seal the stent thus creating a PVP-Sanglifehrin A-PVP sandwich coated stent.

The Sandwich Coating Procedure:

100 mg of PVP is added to a 50 mL Erlenmeyer containing 12.5 ml of chloroform or tetrahydrofuran. The flask was carefully mixed until all of the PVP is dissolved. In a separate clean, dry Erlenmeyer flask 250 mg of Sanglifehrin A is added to 11 ml of the same solvent and mixed until dissolved.

A clean, dried stent is then sprayed with PVP until a smooth confluent polymer layer was achieved. The stent was then dried in a vacuum oven at 50° C. for 30 minutes.

Next, successive layers of Sanglifehrin A are applied to the polymer-coated stent. The stent is allowed to dry between each of the successive Sanglifehrin A coats. After the final Sanglifehrin A coating has dried, three successive coats of PVP are applied to the stent followed by drying the coated stent in a vacuum oven at 50° C. overnight. The dried, coated stent is weighed and its weight recorded.

The concentration of drug in the drug/polymer solution and the final amount of drug loaded onto the stent determine the final coating weight. Final coating weight is calculated by subtracting the stent's pre-coating weight from the weight of the dried, coated stent.

In a similar manner, Sanglifehrin A may be replaced by similar quantities of Sanglifehrin B, Sanglifehrin C, Sanglifehrin D, or pharmaceutically acceptable derivatives thereof.

Example 4

Coating a Clean, Dried Stent with Pure Drug 1.00 g of Sanglifehrin A is carefully weighed and added to a small neck glass bottle containing 12 ml of chloroform or tetrahydrofuran, heated at 50° C. for 15 minutes and then mixed until the Sanglifehrin A is completely dissolved.

Next a clean, dried stent is mounted over the balloon portion of angioplasty balloon catheter assembly. The stent is then sprayed with, or in an alternative embodiment, dipped into, the Sanglifehrin A solution. The coated stent is dried in a vacuum oven at 50° C. overnight. The dried, coated stent was weighed and its weight recorded.

The concentration of drug loaded onto the stents is determined based on the final coating weight. Final coating weight is calculated by subtracting the stent's pre-coating weight from the weight of the dried, coated stent.

In a similar manner, Sanglifehrin A may be replaced by similar quantities of Sanglifehrin B, Sanglifehrin C, Sanglifehrin D, or pharmaceutically acceptable derivatives thereof.

Example 5

In Vivo Testing of a Anti-Inflammatory Agent-Coated Vascular Stent in a Porcine Model The ability of an anti-inflammatory agent to reduce neointimal hyperplasia in response to intravascular stent placement in an acutely injured porcine coronary artery is demonstrated in the following example. Two controls and three treatment arms were used as outlined below:
1. Control Groups:
   Six animals were used in each control group. The first control group tests the anti-restenotic effects of the clean, dried stent having neither polymer nor drug coatings. The second control group tests the anti-restenotic effects of polymer alone. Clean, dried stents having PCL coatings without drug are used in the second control group.
2. Experimental Treatment Groups
   Three different stent configurations and two different drug dosages are evaluated for their anti-restenotic effects. Twelve animals are included in each group.
   Group 1, designated the fast release group, uses stents coated with 50 μg Sanglifehrin A without polymer in accordance with the teachings of the present invention.
   Group 2, designated the slow-release group, uses stents coated with 50 μg of Sanglifehrin A impregnated within a polymer at a Sanglifehrin A to polymer ratio of 1:9 in accordance with the teachings of the present invention.
   Group 3, designated the medium-release group, uses stents coated with 250 μg of Sanglifehrin A impregnated within a polymer at a Sanglifehrin A to polymer ratio of 1:1 in accordance with the teachings of the present invention.

The swine has emerged as the most appropriate model for the study of the endovascular devices. The anatomy and size of the coronary vessels are comparable to that of humans. Furthermore, the neointimal hyperplasia that occurs in response to vascular injury is similar to that seen clinically in humans. Results obtained in the swine animal model are considered predictive of clinical outcomes in humans. Consequently, regulatory agencies have deemed six-month data in the porcine sufficient to allow progression to human trials.

Non-atherosclerotic acutely injured RCA, LAD, and/or LCX arteries of the Farm Swine (or miniswine) are utilized in this study. Placement of coated and control stents is random by animal and by artery. The animals are handled and maintained in accordance with the requirements of the Laboratory Animal Welfare Act (P.L. 89-544) and its 1970 (P.L. 91-579), 1976 (P.L. 94-279), and 1985 (P.L. 99-198) amendments. Compliance is accomplished by conforming to the standards in the Guide for the Care and the Use of Laboratory Animals, ILAR, National Academy Press, revised 1996. A veterinarian performs a physical examination on each animal during the pre-test period to ensure that only healthy pigs are used in this study.

A. Pre-Operative Procedures

The animals are monitored and observed 3 to 5 days prior to experimental use. The animals have their weight estimated at least 3 days prior to the procedure in order to provide appropriate drug dose adjustments for body weight. At least one day before stent placement, 650 mg of aspirin is administered. Animals are fasted twelve hours prior to the procedure.

B. Anesthesia

Anesthesia is induced in the animal using intramuscular Telazol and Xylazine. Atropine is administered (20 μg/kg I.M.) to control respiratory and salivary secretions. Upon induction of light anesthesia, the subject animal is intubated. Isoflurane (0.1 to 5.0% to effect by inhalation) in oxygen is administered to maintain a surgical plane of anesthesia. Continuous electrocardiographic monitoring is performed. An I.V. catheter is placed in the ear vein in case it is necessary to replace lost blood volume. The level of anesthesia is monitored continuously by ECG and the animal's response to stimuli.

C. Catheterization and Stent Placement

Following induction of anesthesia, the surgical access site is shaved and scrubbed with chlorohexidine soap. An incision is made in the region of the right or left femoral (or carotid) artery and betadine solution is applied to the surgical site. An arterial sheath is introduced via an arterial stick or cutdown and the sheath is advanced into the artery. A guiding-catheter is placed into the sheath and advanced via a 0.035" guide wire as needed under fluoroscopic guidance into the ostium of the coronary arteries. An arterial blood sample is obtained for baseline blood gas, ACT and HCT. Heparin (200 units/kg) is administered as needed to achieve and maintain ACT≧300 seconds. Arterial blood pressure, heart rate, and ECG are recorded.

After placement of the guide catheter into the ostium of the appropriate coronary artery, angiographic images of the vessels are obtained in at least two orthagonal views to identify the proper location for the deployment site. Quantitative coronary angiography (QCA) is performed and recorded. Nitroglycerin (200 μg I.C.) is administered prior to treatment and as needed to control arterial vasospasm. The delivery system is prepped by aspirating the balloon with negative pressure for five seconds and by flushing the guidewire lumen with heparinized saline solution.

Deployment, patency and positioning of stent are assessed by angiography and a TIMI score is recorded. Results are recorded on video and cine. Final lumen dimensions are measured with QCA and/or IVUS. These procedures are repeated until a device is implanted in each of the three major coronary arteries of the pig. After final implant, the animal is allowed to recover from anesthesia. Aspirin is administered at 325 mg p.o. qd until sacrifice.

D. Follow-up Procedures and Termination

After 28 days, the animals are anesthetized and a 6 F arterial sheath is introduced and advanced. A 6 F large lumen guiding-catheter (diagnostic guide) is placed into the sheath and advanced over a guide wire under fluoroscopic guidance into the coronary arteries. After placement of the guide catheter into the appropriate coronary ostium, angiographic images of the vessel are taken to evaluate the stented sites. At the end of the re-look procedure, the animal is euthanized with an overdose of Pentabarbitol I.V. and KCL I.V. The heart, kidneys, and liver are harvested and visually examined for any external or internal trauma. The organs are flushed with 1000 ml of lactated ringers at 100 mmHg and then flushed with 1000 ml of formalin at 100-120 mmHg. All organs are stored in labeled containers of formalin solution.

E. Histology and Pathology

The stented vessels are X-rayed prior to histology processing. The stented segments are processed for routine histology, sectioned, and stained following standard histology lab protocols. Appropriate stains are applied in alternate fashion on serial sections through the length of the treated vessels.

F. Data Analysis and Statistics

1. QCA Measurement

Quantitative angiography is performed to measure the balloon size at peak inflation as well as vessel diameter pre- and post-stent placement and at the 28-day follow-up. The following data are measured or calculated from angiographic data:

Stent-to-artery-ratio
Minimum lumen diameter (MLD)
Distal and proximal reference lumen diameter Percent Stenosis=(Minimum lumen diameter÷reference lumen diameter)×100

2. Histomorphometric Analysis

Histologic measurements are made from sections from the native proximal and distal vessel and proximal, middle, and distal portions of the stent. A vessel injury score is calculated using the method described by Schwartz et al. (Schwartz R S et al. Restenosis and the proportional neointimal response to coronary artery injury: results in a porcine model. J Am Coll Cardiol 1992; 19:267-74). The mean injury score for each arterial segment is calculated. Investigators scoring arterial segment and performing histopathology are "blinded" to the device type. The following measurements are determined:

External elastic lamina (EEL) area
Internal elastic lamina (IEL) area
Luminal area
Adventitial area
Mean neointimal thickness
Mean injury score 3. The neointimal area and the % of in-stent restenosis are calculated as follows:

Neointimal area=(IEL−luminal area)

In-stent restenosis=[1−(luminal area÷IEL)]×100.

A given treatment arm will be deemed beneficial if treatment results in a significant reduction in neointimal area and/or in-stent restenosis compared to both the bone stent control and the polymer-on control.

In a similar manner, Sanglifehrin A may be replaced by similar quantities of Sanglifehrin B, Sanglifehrin C, Sanglifehrin D, or pharmaceutically acceptable derivatives thereof.

G. Surgical Supplies and Equipment

The following surgical supplies and equipment are required for the procedures described above:
1. Standard vascular access surgical tray
2. Non-ionic contrast solution
3. ACT machine and accessories
4. HCT machine and accessories (if applicable)
5. Respiratory and hemodynamic monitoring system
6. IPPB Ventilator, associated breathing circuits and Gas Anesthesia Machine
7. Blood gas analysis equipment
8. 0.035" HTF or Wholey modified J guidewire, 0.014" Guidewires
9. 6, 7, 8, and 9 F introducer sheaths and guiding catheters (as applicable)
10. Cineangiography equipment with QCA capabilities
11. Ambulatory defibrillator
12. Standard angioplasty equipment and accessories
13. IVUS equipment (if applicable)
14. For radioactive labeled cell studies (if applicable):
15. Centrifuge
16. Aggregometer
17. Indium 111 oxime or other as specified
18. Automated Platelet Counter
19. Radiation Detection Device Example 6

Inhibition of Inflammatory Cytokine Production by Anti-Inflammatory Agents in Human Coronary Artery Smooth Muscle Cells and in Human Monocytes—In-Vitro Studies A. Materials
1. Human coronary smooth muscles cells (HCASMC) are obtained from Clonetics, a division of Cambrex, Inc.
2. HCASMC basal media is supplied by Clonetics and is supplemented with fetal bovine serum, insulin, hFGF-B (human fibroblast growth factor), and hEGF (human epidermal growth factor).
3. U937 monocyte histiocytic lymphoma cell line obtained from ATCC.
4. U937 growth media consists of the following ingredients: RPMI 1640 basal media supplied by Clonetics and is supplemented with fetal bovine serum, 2 mM L-glutamine, sodium bicarbonate, glucose, HEPES and sodium pyruvate.
5. Reagents for cell stimulation: recombinant human TNF, recombinant human IL-1β and recombinant human PDGF are obtained from R&D Systems. Bacterial synthetic LPS is obtained from Sigma.
6. Sanglifehrin A
7. BD Cytometric Bead Arrays kits; Human Chemokine kit I (cat #552990) and Human Inflammation kit (551811) from BD Biosciences.
8. FACS bioanalyser 'FACS ARRAY' from BD Biosciences.
9. 96-well tissue culture plates B. Study Regarding Inhibition of Inflammatory Cytokine Secretion by Human Coronary Artery Smooth Muscle Cells Human coronary smooth muscles cells (HCASMC) are seeded in 96-well tissue culture plates to reach confluency of 70% (usually $2 \times 10^5$ cells per well) in fully supplemented cell culture media.

The media is substituted for plain media (not supplemented by serum or growth factors) and various concentrations of anti-inflammatory agent Sanglifehrin A is added to cells, which are then stimulated with a 'mixture of inflammation inducing agents' that include, the recombinant pro-inflammatory cytokines IL-1β (10 ng/ml), purified coagulation factors, fXa or Thrombin (10 nM) and Platelet Derived Growth Factor (PDGF, 10 ng/ml), and incubated for 48 hours.

Conditioned media, containing the inflammatory factors secreted by HCASMC, is then collected in a matching 96 well format, and stored at −20° C.

At the time of assay, conditioned media is thawed and the amounts of the secreted cytokines assayed using a FACS bioanalyzer and Human Chemokine and Inflammation kits. The following inflammatory cytokines are quantitatively measured: IL-8, IL-6, MCP-1 and Rantes. The assays are preformed according to manufacturer instructions, shortly, distinct fluorescent beads that have been coated with corresponding capture antibodies (IL-8, IL-6, MCP-1 and Rantes, respectively) are mixed with the test samples/standards and a detection reagent is added (comprising of PE conjugated detection antibodies) for 3 hour incubation. The assay results are then obtained by flow cytometry, using a FACSARRAY Bio-analyzer.

The data analysis is performed using BD™ CBA software.

In a similar manner, Sanglifehrin A may be replaced by similar quantities of Sanglifehrin B, Sanglifehrin C, Sanglifehrin D, or pharmaceutically acceptable derivatives thereof.

C. Study Regarding Inhibition of Inflammatory Cytokine Secretion by Human Monocytes A U937 monocyte histiocytic lymphoma cell line is seeded in 96-well polystyrene tissue culture plates at a concentration of $0.5 \times 10^6$ cells per well in fully supplemented cell culture media. Various concentrations of anti-inflammatory agent Sanglifehrin A is added to cells which are then stimulated with a LPS (0.5 ug/ml) and incubated for 20 hours.

Conditioned media, containing the inflammatory factors secreted by U937 is then collected, in a matching 96 well format, and stored at −20° C.

At the time of assay, conditioned media is thawed and the amounts of the secreted cytokines assayed using a FACS bioanalyzer and Human Chemokine and Inflammation kits. The following inflammatory cytokines are quantitatively measured: TNFα, IL-1β and IL-8. The assays are preformed according to manufacturer instructions, shortly, distinct fluorescent beads that have been coated with corresponding capture antibodies (TNFα, IL-1β and IL-8, respectively) are mixed with the test samples/standards and a detection reagent is added (comprised of PE conjugated detection antibodies) for 3 hour incubation. The assay results are then obtained by flow cytometry using a FACSARRAY Bio-analyzer.

The data analysis is performed using BD™ CBA software.

In a similar manner, Sanglifehrin A may be replaced by similar quantities of Sanglifehrin B, Sanglifehrin C, Sanglifehrin D, or pharmaceutically acceptable derivatives thereof.

Unless otherwise indicated, all numbers expressing quantities of ingredients, properties such as molecular weight, reaction conditions, and so forth used in the specification and claims are to be understood as being modified in all instances by the terms "about" or "approximately." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The terms "a" and "an" and "the" and similar terms used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited patents and printed publications are herein individually incorporated by reference.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

REFERENCES

The following references are incorporated herein in their entirety and are made a part hereof:
PCT Published Application WO 97/02285
PCT Published Application WO 98/07743
Fehr, T.; et al, J. Antibiot. 1999, 52(5): 474
Sanglier, J.-J.; et al, J. Antibiot. 1999 52(5): 466
Zhang, L. H.; et al, J. Biol. Chem. 2001, 276(47): 43534
Clarke, S. J.; et al, J. Biol. Chem. 2002, 277(38): 34793
Allen, A.; et al, J. Immunol. 2004, 172(8): 4797
Woltman, A. M.; et al, J. Immunol. 2004, 172(10): 6482
Steinschulte, C.; et al, Am. J. Transplant 2004, 4 (Suppl. 8): Abst. 129

We claim:

1. An implantable medical device for the inhibition of restenosis coated with an anti-inflammatory agent selected from the group consisting of Sanglifehrin A, Sanglifehrin B, Sanglifehrin C, Sanglifehrin D, and pharmaceutically acceptable derivatives thereof.

2. The medical device according to claim 1 selected from the group consisting of stents, catheters, micro-particles, probes and vascular grafts.

3. The medical device according to claim 2 wherein said stent is an intravascular stent, esophageal stent, urethral stent or biliary stent.

4. The medical device according to claim 3 coated with a biocompatible polymer.

5. An intravascular stent for site-specific, controlled-release delivery of a medicament for the inhibition of restenosis, said stent having a coating comprising a biocompatible polymer and an anti-inflammatory agent selected from the group consisting of Sanglifehrin A, Sanglifehrin B, Sanglifehrin C, Sanglifehrin D, and pharmaceutically acceptable derivatives thereof.

6. The intravascular stent according to claim 5 wherein said coating comprises:

(a) between about 10 μg and 1.0 mg of an anti-inflammatory agent, and
(b) a biocompatible polymer,
wherein said anti-inflammatory agent and said biocompatible polymer are in a ratio relative to each other of between about 1:1 to about 1:10 (w/w).

7. The intravascular stent according to claim 5 wherein said stent has a metallic body.

8. The intravascular stent according to claim 5 wherein said coating comprises at least one additional therapeutic agent.

* * * * *